United States Patent [19]

Kankel et al.

[11] 4,039,639
[45] Aug. 2, 1977

[54] LIQUID ENTRAINING SYSTEM OF THE HUMIDIFIER AND NEBULIZER TYPE

[75] Inventors: Richard L. Kankel, San Jose, Calif.; William G. Brown, Troutdale, Oreg.

[73] Assignee: Richard L. Kankel, San Jose, Calif.

[21] Appl. No.: 566,882

[22] Filed: Apr. 10, 1975

[51] Int. Cl.² .............................................. B01F 3/04
[52] U.S. Cl. ...................... 261/121 R; 261/DIG. 65; 128/194
[58] Field of Search ............... 128/194, 193, 186, 187, 128/188, 145.8, 142, 146.4, 146.5, DIG. 2; 261/DIG. 65, 77 R, 121 R, 78 A; 137/557

[56] References Cited

U.S. PATENT DOCUMENTS

| | | | |
|---|---|---|---|
| 835,075 | 11/1906 | Mahaffy | 128/146.5 |
| 2,102,037 | 12/1937 | Schwartz | 128/146.4 |
| 2,381,568 | 8/1945 | Booharin | 128/146.5 |
| 3,155,110 | 11/1964 | Hoffman | 137/525.1 |
| 3,572,660 | 3/1971 | Mahon | 128/186 X |
| 3,652,015 | 3/1972 | Beall | 239/338 |
| 3,724,454 | 4/1973 | Brown | 128/194 |
| 3,807,445 | 4/1974 | McPhee | 128/188 X |
| 3,822,720 | 7/1974 | Souza | 137/525.1 |
| 3,825,000 | 7/1974 | Huggins | 128/194 |
| 3,846,518 | 11/1974 | McPhee | 128/194 |
| 3,852,385 | 12/1974 | Huggins | 261/DIG. 65 X |
| 3,903,216 | 9/1975 | Allan et al. | 128/186 |
| 3,913,843 | 10/1975 | Cambio | 128/194 |
| 3,944,635 | 3/1976 | Siegenthaler | 128/194 |

Primary Examiner—Robert W. Michell
Assistant Examiner—Henry J. Recla
Attorney, Agent, or Firm—John J. Leavitt

[57] ABSTRACT

Presented are humidifier and nebulizer devices for use in connection with inhalation therapy. Whether used as humidifier or nebulizer the devices are adapted to fit a conventional irrigating container commonly stocked in large numbers by most hospitals.

2 Claims, 8 Drawing Figures

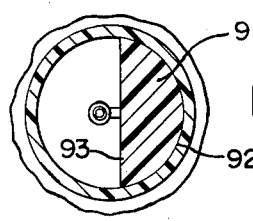
FIG. 6
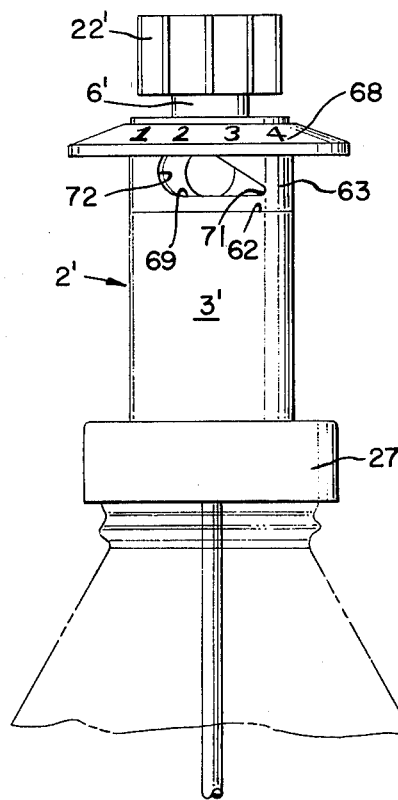
FIG. 4
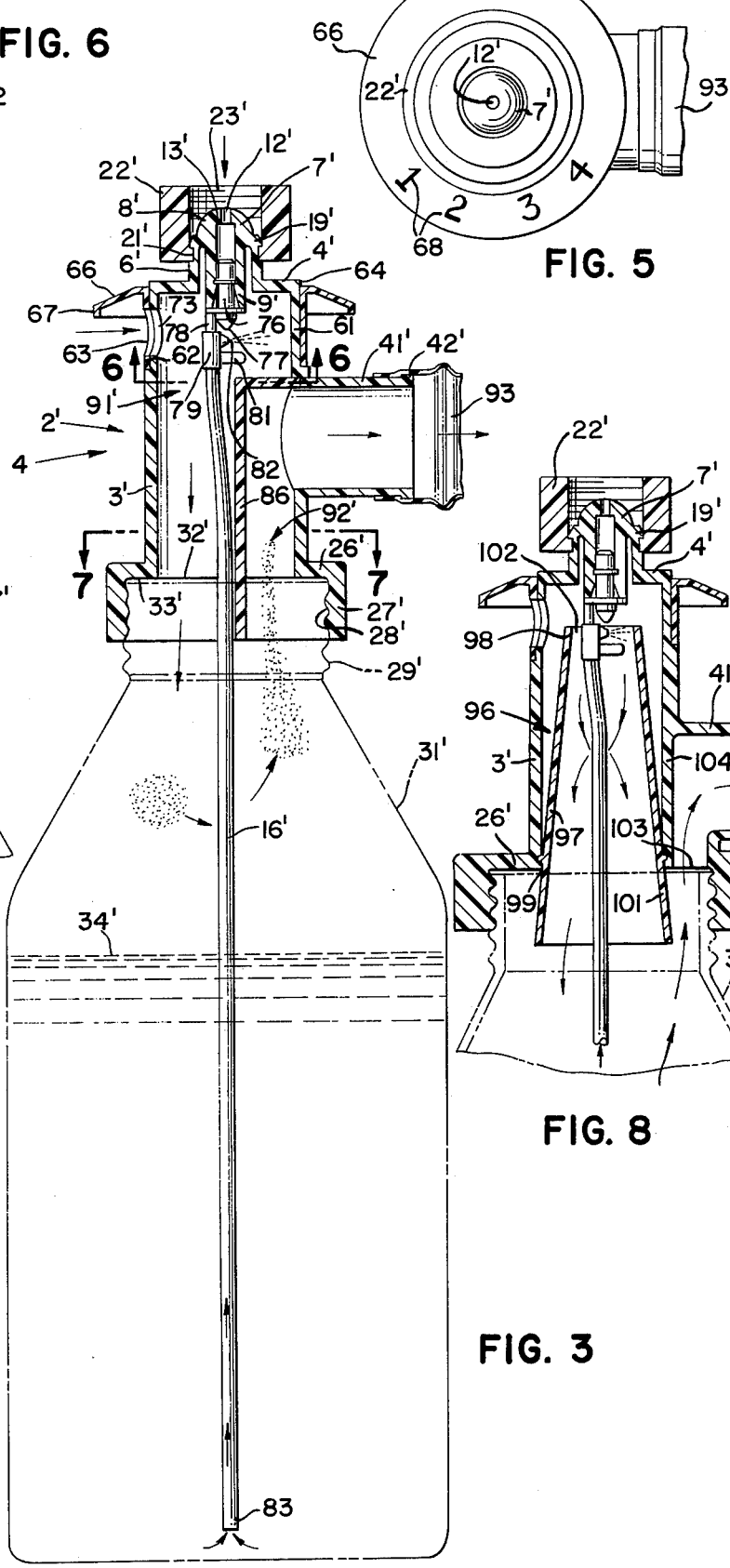
FIG. 3
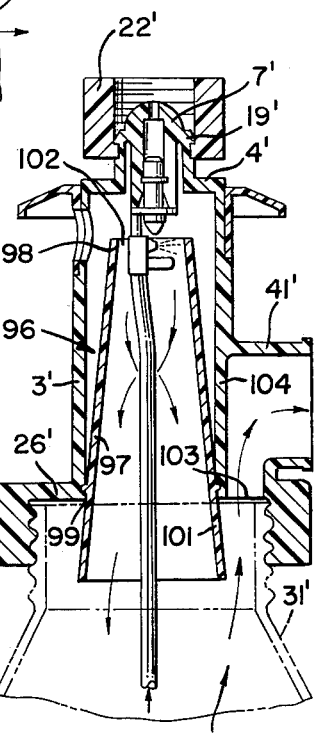
FIG. 5
FIG. 8
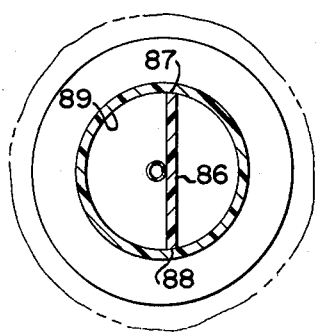
FIG. 7

LIQUID ENTRAINING SYSTEM OF THE HUMIDIFIER AND NEBULIZER TYPE

BACKGROUND OF THE INVENTION

Inhalation therapy is frequently used for patients suffering from such diseases as emphysema, stroke, heart stoppage, drowning, and many other afflictions which a human may suffer which require the administration of either pure oxygen or a high percentage of oxygen or other medicaments administered through inhalation therapy.

One of the problems that is encountered and must be overcome is the necessity of maintaining such medicaments sterile during the administration process. Since the most common inhalation therapy given is the administration of oxygen, either in its pure state or diluted with air, the following description will progress in connection with a humidifier which humidifies pure oxygen as it is taken from an oxygen bottle or other source; and in connection with other types of medicaments, including oxygen, will describe a nebulizer which permits the physician to control the percentage and humidity of oxygen being administered. In each case, the humidifier or nebulizer is designed and constructed so that it may be easily sterilized, packaged in a sterile package which is opened only upon use and applied to a sterile container, thus ensuring the sterility of medicaments being administered to the patient.

Accordingly, it is one of the objects of the present invention to provide a humidifier device which may be applied to the standard screw-threaded sterile irrigating container normally found in most hospitals and which functions to support the container during use.

Another object of the invention is to provide a humidifier structure incorporating an alarm device for alerting hospital personnel of a malfunction in the humidifier.

Conventional humidifiers as found in hospitals and other patient care centers are either of the disposable or non-disposable types. The non-disposable humidifiers require constant cleaning, which is not always done or not done effectively by hospital personnel. The disposable humidifiers are, variously, non-sterile and may or may not be contaminated; prefilled sterile humidifiers which are costly; and humidifiers that adapt to intravenous solution bottles but which do not have a separate support for the bottle when used as a humidifier. Accordingly, it is another object of the invention to provide a humidifier/nebulizer device which obviates the disadvantages of conventional humidifier/nebulizers because it permits hospital personnel to utilize a standard irrigating container as a humidifier or nebulizer, thus insuring the sterility of the oxygen or air being administered to the patient.

Another object of the invention is the provision of a humidifier/nebulizer device equipped with a standard screw cap fitting that may be screwed onto the standard stock irrigating container usually found in large numbers in any hospital, thus forming a support for such bottle as well as insuring the sterility of the contents thereof.

When used as a nebulizer, the device provides a mist-forming jet when the device is connected to a source of oxygen, and also provides for adjustment of the quantity of oxygen being administered to the patient. Another object of the invention is the provision of a nebulizer structure incorporating a baffle which increases the therapeutic affect of the medicament being administered by refining the mist particles administered to the patient.

The invention possesses other objects and features of advantage, some of which, with the foregoing, will be apparent from the following description and the drawings. It is to be understood, however, that the invention is not limited to the embodiments illustrated and described, since the invention may be embodied in various forms within the scope of the appended claims.

SUMMARY OF THE INVENTION

In terms of broad inclusion, in one aspect of the invention, the humidifier comprises a sterilizable hollow body having attachment means at one end for attachment of the body to a source of oxygen under pressure, while at the opposite end the hollow body may be screwed onto the conventional irrigating solution bottle commonly found in hospitals. Diffusion means are connected to the inlet port of the hollow body to effect discharge of oxygen under pressure below the surface of sterile water contained in the irrigating solution bottle. Means are also provided on the hollow body constituting an outlet port for humidified oxygen in gaseous form for delivery to the patient. Means are also provided on the hollow body to sound an alarm in the event the pressure builds up in the outlet port to a dangerous level. In its other aspect, namely, that of a nebulizer, the hollow body is provided with a jet structure for atomizing water or some other medicament contained in a conventional irrigating container and which is discharged into the interior of the hollow body of the nebulizer device through the action of atmospheric pressure on the one hand and a reduction in pressure caused by the passage of oxygen through a Venturi tube, thus causing water or other medicament contained in the irrigating container to pass upwardly through a discharge tube and to be disseminated in the path of oxygen entering into the system. An outlet port is provided for discharge of humidified oxygen or other oxygenized medicament to the patient, and baffle means are provided within the hollow nebulizer body separating the outlet port of the body from the remainder thereof which in effect constitutes a mixing chamber for the humidified oxygen.

BRIEF DESCRIPTION OF THE DRAWINGS

FIG. 3 is a vertical cross-sectional view of the nebulizer device shown attached to a conventional irrigation solution bottle shown in broken lines.

FIG. 4 is an elevational view of the nebulizer device shown in FIG. 3 and taken in the direction of the arrow 4.

FIG. 5 is a plan view of the nebulizer device shown in FIGS. 3 and 4.

FIG. 6 is a horizontal cross-sectional view taken in the plane indicated by the line 6—6 in FIG. 3.

FIG. 7 is a horizontal cross-sectional view taken in the plane indicated by the line 7—7 in FIG. 3.

FIG. 8 is a cross-sectional view of another embodiment of the nebulizer device.

DESCRIPTION OF THE PREFERRED EMBODIMENT

Figure 1:
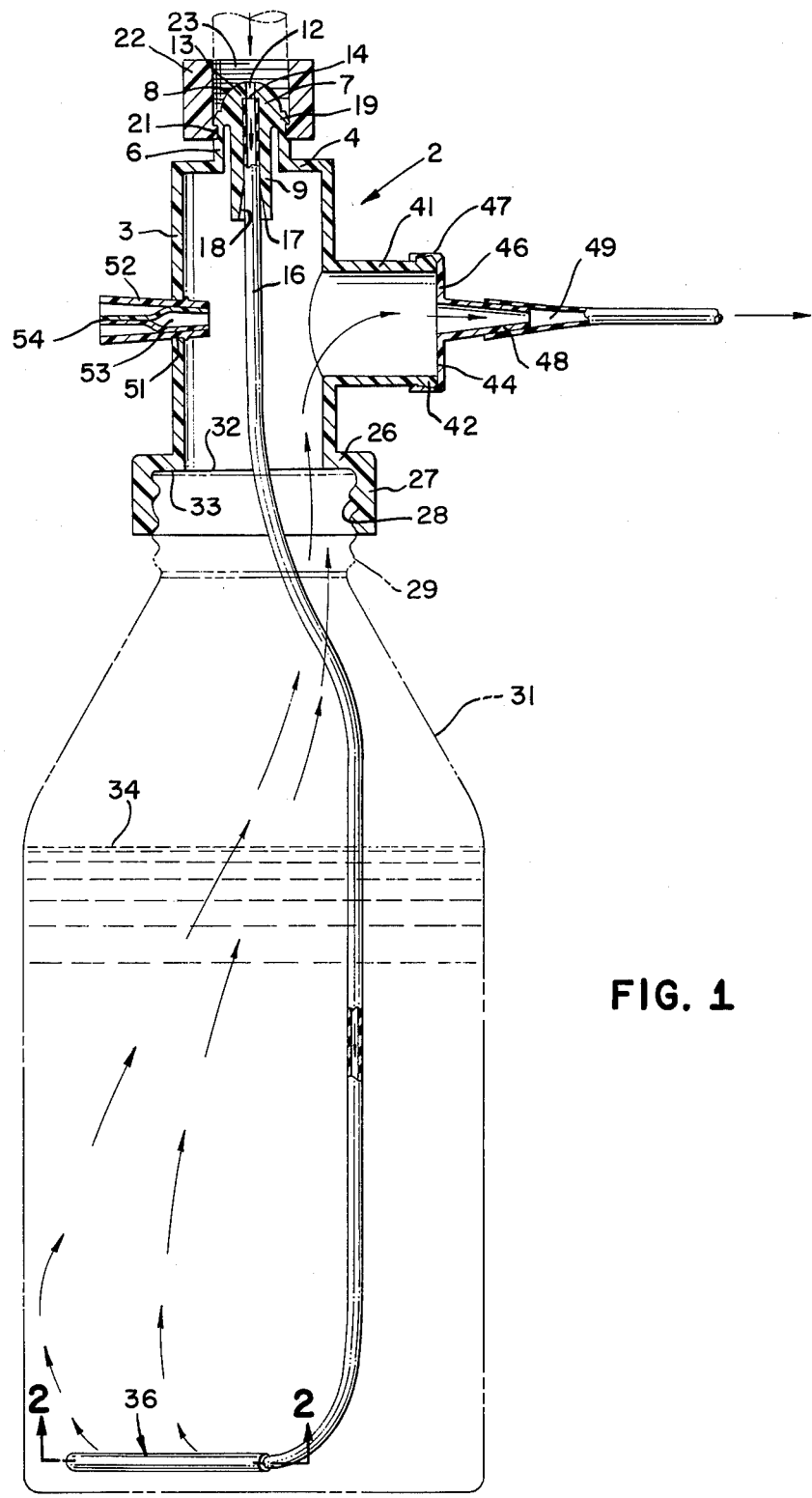
FIG. 1 is a vertical cross-sectional view through the humidifier device of the invention, shown attached to a conventional irrigating container shown in broken lines.
Figure 2:
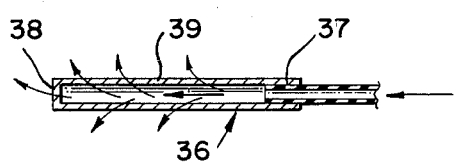
FIG. 2 is a vertical cross-sectional view taken in the plane indicated by the line 2—2 in FIG. 1 and showing the construction of the defusion device fitted to the discharge end of the oxygen inlet tube.

In terms of greater detail, and referring specifically to FIGS. 1 and 2 relating to the humidifier device, the invention as there illustrated comprises a hollow shell designated generally by the numeral 2 and having generally cylindrical side walls 3 formed at one end with a transversely extending wall portion 4 annular in configuration and having an inner perihery which is joined integrally by a reduced-in-diameter cylindrical wall portion 6 terminating in a bulbous end portion 7 having a convex sealing surface 8 and a downwardly projecting cylindrical portion 9, the bulbous portion 7 and the downwardly projecting cylindrical extension 9 being integral and provided with a bore 12 that extends generally axially through the cylindrical extension 9 and in general follows the longitudinal axis of the cylindrical walls 3 of the shell 2.

At its lower end, the bore 12 is increased in diameter to provide shoulders 13 against which may rest the end 14 of an elongated plastic tube 16 inserted into the bore 12 from the inner end thereof. To facilitate insertion of the plastic tube into the enlarged bore section, the bore adjacent the lower end 17 of the extension 9 is provided with a chamfered section 18 as shown which helps guide the end of the tube into the bore. To retain the tube in the bore, all that is required is that the tube be pushed snugly into the bore whereupon frictional resistance between the outer surface of the tube and the inner surface of the bore retain the tube in position.

To attach the shell 2 to a source of oxygen under pressure, the bulbous portion 7 is provided with a generally cylindrical flange 19 below which is engaged a lock flange 21 forming part of a gland 22 having internal threads 23 therein for attachment to the outlet fitting of a source of oxygen.

At its other end, the shell 2 is provided with an annular transversely extending wall section 26 which merges integrally with a cylindrical section 27 having internal threads 28 adapted to engage the external threads 29 formed on the neck portion of a conventional irrigation solution container or bottle 31. The upper end 32 of the container seats against the inner surface 33 of the transversely extending wall portion 26, thus forming a seal between the interior of the shell 2 and the interior of the sterile container 31. As shown in FIG. 1, the flexible plastic tube 16 extends downwardly through the interior of the hollow shell 2, passes into the container 31 and below the surface 34 of liquid contained therein, the liquid conventionally being sterile water. Below the surface of the water, at the discharge end of the tube 16, the tube is provided with a high porosity filter 36 open at one end 37 so that it may be slipped over the discharge end of the tube and held thereon by friction between the two members, while being closed at its opposite end 38 so that oxygen under pressure delivered through the tube 16 passes radially outwardly through the porous walls 39 of the filter. In this way, the oxygen being discharged below the surface of the liquid is preliminarily dispersed over a larger area prior to its coming in contact with the water within the container, thus increasing the humidity of the oxygen as it passes upwardly in the direction of the arrows and exists through a laterally directed outlet nipple 41, generally cylindrical in cross-section and provided with a bead 42 adjacent its outer end 44 for attachment of a cap 46, the flange 47 of which snaps over the bead to lock the cap on the outlet nipple. Centrally disposed on the cap 46 is a generally conical nipple 48 over which may be slipped one end of a delivery tube 49 connected to conventional breathing apparatus used by the patient.

It sometimes happens that the delivery tube 49, which may be three or four feet long, develops a kink and thereby interrupts the flow of humidified oxygen to the patient. When this occurs, a dangerous condition may be created in that the humidifier and container 31, being connected to a source of high pressure oxygen, will build up pressure on the interior thereof which may then be subject to a sudden release of the humidified oxygen under excessive pressure into the respiration apparatus being used by the patient. To preclude this possibility, there is provided on the hollow shell 2, an aperture 51 in which is frictionally engaged a hollow generally conical tubular member 52 within which is molded a valve structure 53 the outer end of which constitutes a flap valve 54 that permits the release of excessive pressure within the humidifier shell. It is important that the fact of an over-pressure occurence be communicated to supervisory personnel within the hospital or within the patient care center. For this purpose, the flap valve 54 constitutes two layers of flexible material joined only along the longitudinal edges to permit the escape of humidified oxygen between the two layers. The passage of oxygen causes the two layers to vibrate and create a staccato sound to signifiy a malfunction.

It will thus be seen that the humidifier device illustrated in FIG. 1 is self-supporting in that it may be manufactured, sterilized and enclosed in a sterile package, and when removed from the sterile package, may immediately be fastened to the sterile container 31, thus maintaining a sterile condition of the humidifier at all times to minimize the possibility of contamination of the patient. Additionally, because of its construction, the humidifier shell 2 may be attached directly to an oxygen tank, or to appropriate high pressure tubing connected to a source of oxygen at some remote location.

Referring to FIGS. 3 through 7, the nebulizer device there illustrated utilized substantially the same basic shell and for this reason, and in the interest of brevity, the same reference numbers used in conjunction with the shell in FIG. 1 are again used in FIG. 3, with the addition of primes.

The shell 2 as viewed in FIG. 3 is modified somewhat by having its upper wall section 61 slightly reduced in thickness to provide a shoulder 62 upon which may rest a circumscribing cylindrical flange 63 constituting a collar held in place by a slightly projecting flange or rib 64 formed adjacent the transverse wall 4'. Integral with the upper end of the cylindrical flange 63 is a radially outwardly projecting flange 66 having a down-turned lip 67 having indicia 68 molded, embossed or otherwise indicated on its upper surface as illustrated in FIGS. 4 and 5. The cylindrical flange 63 is provided with a specially configured aperture 69 generally triangular in configuration, diverging from an apex end 71 to a base end 72. The flange 63 is rotatable on the reduced in diameter wall section 61 which is provided with an aperture 73 similar to the aperture 51 in the shell 2 in FIG. 1, so that the aperture 73 may be completely open, or may be closed to any degree desired by the physician for purposes which will hereinafter be explained.

As illustrated in FIG. 3, instead of inserting the inner end of the tube 16' directly into the bore 12 as was done with the humidifier structure of FIG. 1, there is inserted into the bore 12 a Venturi sleeve 76 having an outlet or discharge orifice 77 in the bottom end thereof through which oxygen under pressure is discharged into the interior of the hollow shell 2'. Suspended from the Venturi sleeve by a support post 78 is a hollow sleeve 79 having an abutment 81 formed on the exterior thereof and extending transversely therefrom and underlying the discharge orifice 77 through which the oxygen enters the shell. Also formed in the sleeve 79 is a discharge orifice 82 through which sterile water or other medicament in solution is discharged in a transverse direction in the manner indicated by the broken lines. The discharge orifice 82 is also in position to discharge liquid into the path of oxygen being discharged from the discharge orifice of the Venturi tube 76. As shown, the inner end of tube 16' is inserted into the lower end of the tubular sleeve 79 and is retained therein by friction. The tube 16' extends downwardly from the sleeve 79, passes through the neck of the container, and the discharge end 83 thereof is in position to receive the ingress of fluid into the tube so that it may be discharged through the orifice 82.

Baffle means are also provided within the hollow shell as shown in FIGS. 3, 6 and 7. The baffle comprises an elongated member 86 in the nature of a flat plate that extends longitudinally substantially parallel to the longitudinal axis of the shell 2', and extends diametrically across the interior thereof so that the lateral edges 87 and 88 are either integral with the inside surface 89 of the tubular shell or are sealingly engaged thereto in some suitable manner. At its upper end, the baffle includes a transversely extending generally flat semi-circular plate portion 91, the curved periphery 92 of which is integral with or sealed to the inner periphery of the cylndrical wall 3', and the chord 93 of which is integral with the plate portion 86. As illustrated in FIG. 3, the plate portion 91 of the baffle is sealed or impinges against the inner wall surface 89 of the cylindrical tube 3' above the outlet opening or passageway defined by the outlet nipple 41'. Thus, the baffle structure including vertical plate 86 and transverse plate 91 divides the interior of the shell structure into a mixing chamber defined generally by the numeral 91' and including all of that portion of the interior of the shell 2' surrounding the Venturi sleeve 76, the sleeve 79, and that portion of the shell not enclosed by the baffle plates 86 and 91. The remaining portion of the interior of the shell may be defined as a discharge section or area designated generally by the numeral 92' and communicating with the interior of the outlet nipple 41'.

In use, the embodiment of the invention illustrated in FIG. 3 is first removed from a sterile container such as a cellophane bag and immediately attached to a conventional irrigation solution bottle containing an appropriate medicament or containing sterile water. The tube 16' extends downwardly into the sterile medicament or water, and the flange 22' is connected to a source of oxygen under pressure. Thereafter, a flexible tubing 93 connected to appropriate respiratory apparaus in use by the patient is slipped over the outlet nipple 41' and the physician or nurse or other supervisory personnel in attendance adjusts the collar including flange 63 so that the aperture 69 registers with the aperture 73 in such a way as to provide the proper proportion of air to oxygen within the interior of the shell.

Oxygen discharged from the orifice 77 which constitutes the outlet end of the Venturi causes a reduction in pressure to below atmospheric pressure in the immediate vicinity of the orifice 82, thus resulting in atmospheric pressure within the container causing liquid to flow upwardly through the tube 16' and to be discharged through the orifice 82. As the liquid is discharged through the orifice 82, the stream of oxygen being discharged through the orifice 77 blasts the stream of liquid, causing it to impinge against and be dispersed by the abutment 81 immediately below the orifice 82. In this manner, the dispersed oxygen and liquid is caused to intermingle in the form of a mist which is then carried downwardly through the chamber 91' of the shell where it passes in the direction of the arrows to collect in the portion or chamber of the sterile container 31 above the liquid 34' in the form of a mist or cloud of humidified oxygen or oxygen mixed with some other appropriate medicament. Thereafter, such oxygen in mist form is drawn outwardly in the direction of the arrows and passes upwardly through that portion of the shell enclosed by the baffle plates 86 and 91 and thus enters the outlet nipple 41' from whence it is drawn on demand by the patient.

In FIG. 8, there is shown a different embodiment of the nebulizer device illustrated in FIG. 3, one of the changes constituting a different type of baffle designated generally by the numeral 96 and comprising a thin wall shell 97 in the form of a hollow cone the apex end 98 of which surrounds the orifice 82 and the discharge end of the Venturi sleeve 76. The base end of the hollow conical shell sealingly engages the inner peripheral corner 99 of the transverse wall 26' as shown, and is provided with a short skirt portion 101 that projects downwardly into the neck of the irrigation solution container 31'. Since the engagement at the corner 99 is complete through 360°, it will be noted that ambient air entering the aperture 73 must pass through the open apex end 102 of the cone and then pass downwardly through the cone, carrying the oxygenated mist downwardly into the upper portion of the container. The oxygenated mist then passes upwardly on the outside of the baffle 96, through an opening 103 formed in the transverse wall 26', and from there passes outwardly through the outlet nipple 41' as before. To insure that oxygenated mist or medicament passes downwardly through the cone and is discharged into the container prior to being dispensed through the nipple 41', the wall 3' of the shell is continued downwardly in a portion 104 opposite the passageway formed by the outlet nipple 41', thus forcing the oxygenated mist to pass downwardly through the cone into the upper portion of the sterile container above the liquid contained therein, and from there to be drawn on demand by the patient.

It will thus be seen that the humidifier/nebulizer devices may each be individually wrapped in a sterile container or package and opened only at the instant that it is to be applied to the conventional and sterilized irrigation container. In this way, maximum safety is afforded the patient against the danger of contamination.

Having thus described the invention, what is claimed to be new and novel and desired to be covered by United States letters patent is as follow:

1. An oxygen humidifier device for use in conjunction with a conventional irrigating container having a threaded neck portion and on which the oxygen humidifier device may be threadably mounted for administering inhalation therapy to a patient, comprising:
  a. an elongated, generally cylindrical hollow shell having a vertically extending longitudinal axis, said shell including at its lower end a first threaded gland adapted to be sealingly secured by threaded engagement to the threaded neck of the container so that the hollow interior of the shell communicates with the interior of the container;

b. connector means on the upper end of the hollow shell including a second threaded gland rotatably mounted on an upwardly extending generally cylindrical bulbous extension of said shell, said extension having an upper convex sealing surface adapted to engage a source of oxygen and said gland being adapted to sealingly attach the source of oxygen to said shell;

c. a restricted passageway through said bulbous extension communicating the interior of the hollow shell with the exterior thereof and adapted for connecting said source of oxygen to the interior of said shell;

d. an oxygen diffuser adapted to be immersed in liquid contained in said container when said hollow shell is sealingly secured to the threaded neck of the container;

e. a downwardly projecting cylindrical extension integral with and extending generally axially through said bulbous extension, said downwardly projecting extension having a bore which is an extension of said restricted passage, the lower end of said bore having an increased diameter portion defining an integral interior shoulder;

f. flexible tube means connected at one end to said diffuser, the other end being inserted into said bore to engage said interior shoulder, said tube means connecting said diffuser to said restricted passageway so as to convey oxygen under pressure to said diffuser;

g. means including a chamfered portion within said bore to secure said flexible tube means;

h. an outlet nipple in said shell for discharging humidified oxygen to the patient upon demand thereby, said outlet nipple comprising a laterally directed, generally cylindrical opening intermediate the upper and lower ends of said shell;

i. cap means mounted on said outlet nipple, said cap means including a centrally disposed conical nipple adapted to receive an oxygen delivery tube; and j. pressure relief valve means on the shell operative to relieve the internal pressure of said humidified oxygen within the shell when such pressure exceeds a predetermined value, said relief valve comprising a generally tubular housing and flap valve means constituting two layers of flexible material secured in said housing and joined along their longitudinal edges to permit the escape of humidified oxygen to produce an audible alarm in the event excessive pressure occurs in said humidifier device, said pressure relief valve being located in the wall of said shell generally intermedite the ends thereof and opposite said outlet nipple.

2. The combination according to claim 1, in which said diffuser comprises an elongated hollow body closed at one end and open at the other end and having porous side walls.

* * * * *